US011382678B1

(12) United States Patent
Haidukewych

(10) Patent No.: US 11,382,678 B1
(45) Date of Patent: Jul. 12, 2022

(54) PERCUTANEOUS METHOD FOR REMOVING AN OUTER PORTION OF THE PROXIMAL END OF A LAG SCREW PROTRUDING FORM A FRACTURED FEMUR

(71) Applicant: George J. Haidukewych, Orlando, FL (US)

(72) Inventor: George J. Haidukewych, Orlando, FL (US)

(*) Notice: Subject to any disclaimer, the term of this patent is extended or adjusted under 35 U.S.C. 154(b) by 88 days.

(21) Appl. No.: 16/501,850

(22) Filed: Jun. 18, 2019

(51) Int. Cl.
A61B 17/92 (2006.01)
A61B 17/74 (2006.01)
A61B 17/72 (2006.01)
A61B 17/56 (2006.01)
A61B 17/90 (2006.01)

(52) U.S. Cl.
CPC ............ *A61B 17/92* (2013.01); *A61B 17/725* (2013.01); *A61B 17/744* (2013.01); *A61B 17/90* (2021.08); *A61B 2017/564* (2013.01)

(58) Field of Classification Search
CPC ..... A61B 17/92; A61B 17/742; A61B 17/744; A61B 17/725
See application file for complete search history.

(56) References Cited

U.S. PATENT DOCUMENTS 5,941,885 A * 8/1999 Jackson ............. A61B 17/7082
606/104
2006/0217711 A1* 9/2006 Stevens ............. A61B 17/8047
606/60

* cited by examiner

Primary Examiner — Julianna N Harvey
(74) Attorney, Agent, or Firm — Arthur W Fisher, III

(57) ABSTRACT

A percutaneous method for removing an outer portion of the proximal end of a lag screw protruding from a fractured femur when embedded in the femur to stabilize an intramedullary nail implanted in the intramedullary canal using a multi-part cannulated driver wherein the lag screw comprises a distal section, an intermediate section including a channel formed in the proximal portion thereof with a driver recess formed at the distal end thereof, and a proximal section having a notch, groove or score mark formed on the exterior surface of the lag screw separating or between the intermediate section and the proximal section and the multi-part cannulated driver comprises a cannulated shaft including a first driver member formed thereon configured to engage the driver recess to prevent the distal section and intermediate section of the lag screw from rotating in the femoral head when torque is applied to the proximal section by a second driver member engaging the proximal section of the lag screw to separate the proximal section from the section and the intermediate section along the notch, groove or score mark.

2 Claims, 7 Drawing Sheets

US 11,382,678 B1

PERCUTANEOUS METHOD FOR REMOVING AN OUTER PORTION OF THE PROXIMAL END OF A LAG SCREW PROTRUDING FORM A FRACTURED FEMUR

BACKGROUND OF THE INVENTION

Field of the Invention

A percutaneous method for removing a portion of the proximal end of a lag screw protruding from the femur when embedded to stabilize an intramedullary nail in the intramedullary canal of the femur.

Description of the Prior Art

Numerous lag screws and lag screw/driver combinations have been designed as implants to compress bone fractures or to stabilize intramedullary nail implants.

Lag screw fixation is a technique used in surgical treatment)internal fixation) of fractures or broken bones. The method or technique often involves the use of half threaded orthopedic bone screws, which are smooth from the head up to half or two-thirds of their length. Even a fully threaded cortical screw can be used as a lag screw if the proximal cortex is over drilled. The function of a lag screw is to achieve compression between the fracture fragments (pieces of bone), which aids in providing lag screw strength for better bone fracture healing.

The threads of the lag screw engage in the distal (away from the insertion point) piece of bone and secure the bone firmly. Thus, this portion of bone can be controlled by moving the head of the lag screw. The smooth portion of the lag screw passes through the proximal fragment of bone and hence, this piece is free to slide along the shaft of the screw. However, the head of the screw serves as a stopper to restrict this motion. When the lag screw is tightened, the head fits snugly on the entry point of the screw and forces the proximal fragment over the distal fragment. Thus, the two (2) fragments of bone are not just aligned but compressed over each other. This provides tremendous lag screw strength for stabilization of broken bones and also for earlier and better bone fracture healing. Examples of the prior art are described below:

U.S. Pat. No. 3,842,824 discloses a multi-section surgical pin to hold a femur fracture together in combination with breaking tool. The intermediate portion or section of the multi-section surgical pin includes a plurality of weakened portions or notches. As each pin is surgically placed in the femur, any portion of the pin projecting outwardly from the bone is removed. This is accomplished by placing the breaking tool over the pin until the distal end of the breaking tool engages the femur. The surgeon then simply bends the proximal portion of the pin separating the proximal portion of the pin from the inserted distal portion of the pin at the weakened portion or notch closest to the external surface of the femur.

U.S. Pat. No. 4,858,601 describes an adjustable two section compression bone screw comprising a shaft having a first and second section each with an external screw thread that can be rotated together as a unit or separately independent of each other. The screw includes means to receive a first driving tool to drive the first and second sections together as a unit or to receive a second driving tool for rotating the second section independently of the first section. In operation, the surgeon rotates the screw sections together as a unit until the first and second sections are imbedded in the first and second bone fragments and the entire device is buried within the bone substance. Then the surgeon removes the first driving tool and inserts the second driving tool into a socket formed on the second section. The second driving tool thus engages only the second section leaving the first section fixed in the first bone fragment. At this point a gap exists between the bone fragments. The gap is narrowed by employing the second driving tool to rotate only the second section in a direction opposite to the direction of rotation wherein the screw was driven into the bone fragments. Since the first section is substantially fixed within the first fragment, the second bone fragment must necessarily be drawn towards and more closely adjacent and into compression with the first bone fragment and the gap between them is narrowed. Thus, the surgeon is provided with a mechanism that allows the first and second bone fragments to be brought adjustably into compression.

U.S. Pat. No. 9,498,229 show a multi-use screw driver for use with a compression screw to implant an adjustable orthopedic compression screw including a depth indicia. The multi-use screw driver comprises a handle, an adjustable head driver and a shaft driver. The shaft driver is concentrically disposed in the adjustable head driver. The adjustable head driver has a lengthwise bore extending therethrough sized and configured to receive the shaft driver while allowing the shaft driver to selectively slide within the adjustable head driver. When the distal tip of the shaft driver is substantially even with the distal tip of the adjustable head driver, the adjustable head driver and shaft driver cooperatively drive the adjustable head and the screw shaft. Thus, the screw driver causes primary compression of the adjustable screw. On the other hand, when the shaft driver is in a retracted position, the distal tip of the shaft driver is recessed in the adjustable driver head to allow the adjustable head driver to drive the adjustable head without the shaft driver driving the screw shaft. Thus, when in the retracted driving position, the screw driver can be used to achieve secondary compression of the adjustable compression screw.

U.S. Pat. No. 8,308,783 depicts a collapsible bone screw for healing bone fragments across a bone fracture including an externally threaded inner screw member and an externally threaded outer screw member including an unthreaded portion. The collapsible bone screw may effectively shorten in length as the two screw members slide, telescope or otherwise axially move toward each other to shorten the overall length thereby preventing any portion of the screw apparatus from protruding from the bone.

Additional examples of the prior art are found in: U.S. Pat. Nos. 5,429,641; 5,498,265; 5,531,748; 6,416,324; 9,060,824; 9,161,790; and 9,980,762.

While some of the prior art may contain some similarities relating to the present invention, none teaches, suggests or includes all of the advantages and unique features of the invention disclosed hereafter.

SUMMARY OF THE INVENTION

The present invention relates to a percutaneous method for removing a portion of the proximal end of a lag screw protruding from a fractured femur.

The lag screw comprises a distal section, an intermediate section including a first channel formed in the proximal portion thereof with a driver recess formed in the distal end thereof and a proximal section including a second channel formed therethrough. At least one groove, notch or score mark formed on the exterior of the lag screw separates the intermediate section from the proximal section.

When the intramedullary nail is implanted in the intramedullary canal and the lag screw is properly embedded in the femur the entire lag screw including the proximal section is substantially disposed within the fractured femur.

As the fracture heals, the fractured portions of the femur are drawn together which may cause at least a portion of the proximal section to protrude from the femur potentially causing pain due to prominence of the lag screw from the femur.

The first channel includes a first driver engagement member or element formed on the inner end portion thereof configured to receive a first or inner driver member as described hereinafter.

The second channel includes a second driver engagement member or element configured to receive a second or outer drive member as described hereinafter.

The groove, notch or score mark or is formed between the intermediate section and the proximal section to weaken the wall of the lag screw to allow separation of the of the proximate section from the intermediate section when the proximal section is twisted or rotated by the driver to exert a torque on the proximal section breaking or separating the proximal section from the externally threaded distal section and the intermediate section.

The driver comprises a cannulated shaft having a passageway and including the first or inner driver member to engage the first driver engagement member and the second or outer drive member rotatably disposed on the cannulated shaft to press-fit into the proximal section to apply torque to the groove, notch or score mark to separate the proximal section from the externally threaded distal section and the intermediate section.

The percutaneous method of removing the outer portion of the proximal end of a lag screw comprises the steps of:
- making a small incision in the skin adjacent proximal end of the lag screw,
- inserting a guide wire through incision and into the lag screw,
- aligning the passageway of the cannulated shaft with the guide wire,
- sliding the cannulated shaft of the driver along the guide wire until the first or inner drive member engages the first driver engagement member or element and press-fitting at least a portion of the second or outer drive member within the proximal section,
- removing the guide wire from the patient,
- holding the cannulated shaft stationary to prevent the intermediate section and distal section from rotating,
- twisting or rotating the second or outer drive member relative to the intermediate section and distal section to generate a torque to break or separate the proximal section from the intermediate section and distal section of the lag screw along the groove, notch or score mark,
- withdrawing the driver and separated proximal section of the lag screw from the patient, and
- closing the incision.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

The present invention relates to a percutaneous method for removing a portion of the proximal end of a lag screw protruding from a fractured femur.

Figure 1:
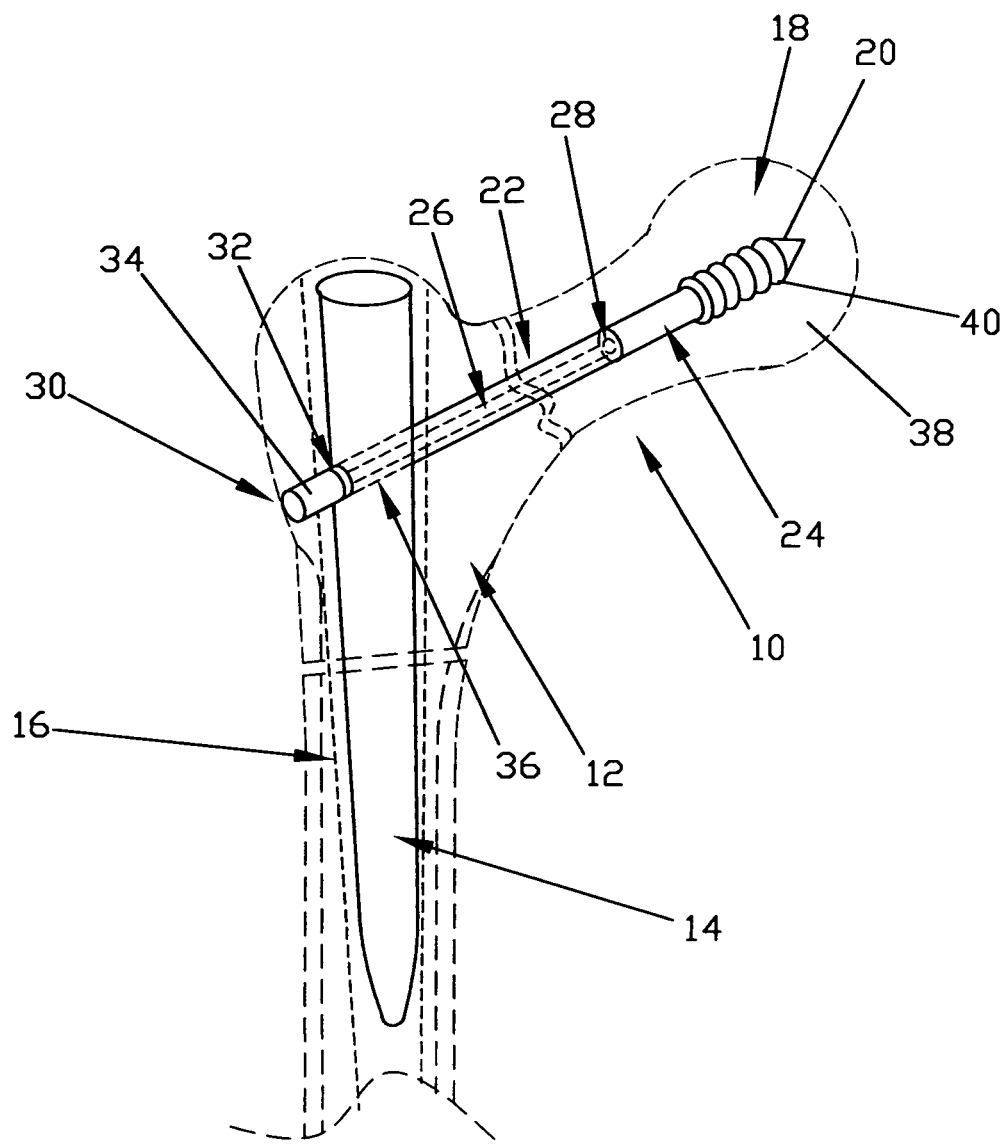
FIG. 1 is a prospective view of the lag screw of the present invention embedded in a fractured femur to stabilize an intramedullary nail implanted in the fractured femur.

As shown in FIG. 1, a lag screw generally indicated as 10 is embedded in a fractured femur generally indicated as 12 to stabilize an intramedullary nail generally indicated as 14 disposed or implanted within the intramedullary canal 16 of the fractured femur 12.

The lag screw 10 comprises an externally threaded distal section generally indicated as 18 having a tip 20 formed on the outer end thereof, an intermediate section generally indicated as 22 having a substantially smooth surface 24 and including a first channel 26 formed in the proximal portion thereof with a driver engagement member or element 28 formed in the distal end thereof, and a proximal section generally indicated 30. At least one groove, notch or score mark 32 formed on the exterior surface 34 of the lag screw 10 separates the intermediate section 22 from the proximal section 30.

As shown in FIG. 1, when the intramedullary nail 14 is implanted in the intramedullary canal 16 and the lag screw 10 is passed through a hole 36 formed in the intramedullary nail 14 and into the femoral head 38 of the femur 12 the entire lag screw 10 including the proximal section 30 is substantially disposed within the fractured femur 12.

Figure 2:
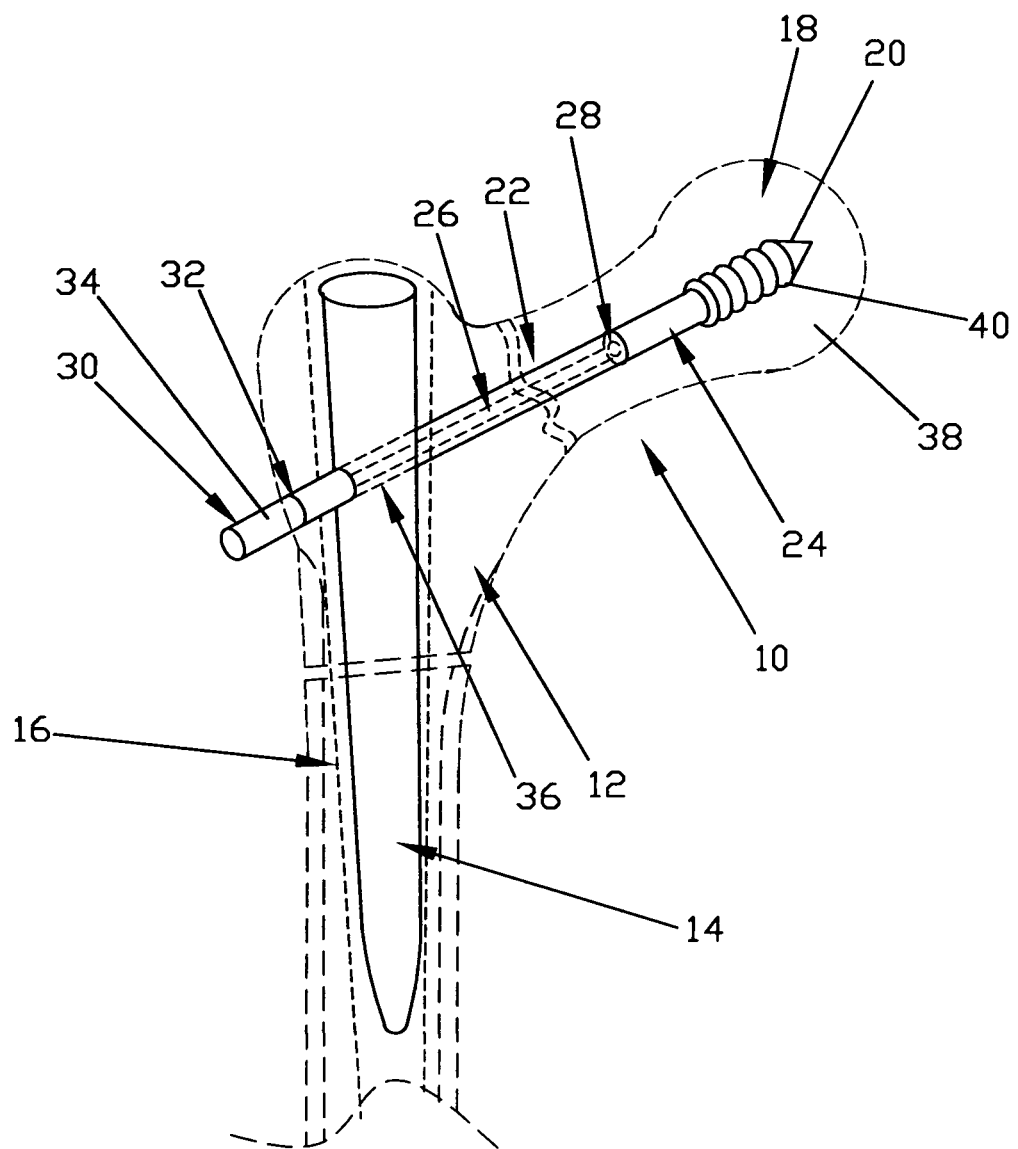
FIG. 2 is a perspective view of the lag screw of the present invention with the proximal section protruding from the intramedullary nail.

As the fracture heals, the fractured portions of the femur 12 are drawn together as shown in FIG. 2 that may cause at least a portion of the proximal section 30 of the lag screw 10 to protrude from the femur 12 potentially causing pain due to prominence of the lag screw 10 from the femur 12.

Figure 3:
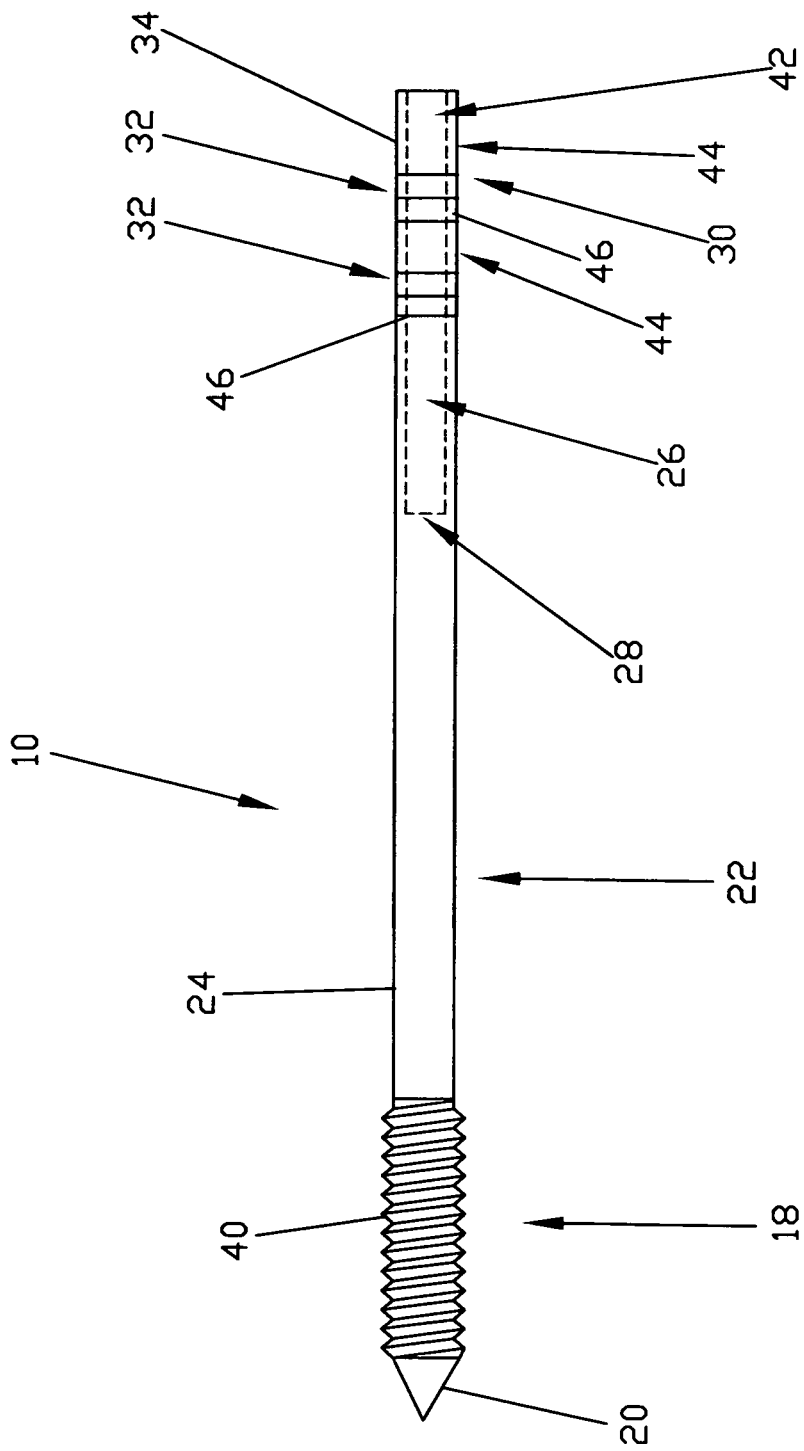
FIG. 3 is a side view of the multi-part lag screw of the present invention.

As shown in FIG. 3, the lag screw 10 comprises the distal section 12, intermediate section 22 and proximal section 30. The distal section 12 comprises the external threads 40 and tip 20 configured to be secured in a channel tapped into the femur femoral head 38. The intermediate section 22 includes the smooth exterior surface 24 configured to be at least partially disposed within the channel 36 formed through the upper portion of the intramedullary nail 14.

The first channel 26 is formed on the proximal end of the intermediate section 22 having a first driver engagement member or element 28 formed on the inner end of the channel 26 in the shape of a flat head slot, phillips head slot, hexagonal slot or similar configuration to receive a first or inner driver member described hereinafter.

Finally, the proximate section 30 includes a second channel 42 coaxially aligned with the first channel 26 of the intermediate section 22.

As previously described, the groove, notch or score mark 32 separates the intermediate section 22 and the proximal section 30 to weaken the wall of the lag screw 10 to allow separation of the proximate section 30 from the intermediate section 22 when the proximal section 30 is twisted or rotated by the driver to exert a torque on the proximal section 30 breaking or separating the proximal section 30 from the externally threaded distal section 18 and the intermediate section or section 22. An indicia 46 such as metallic ring or other material disposed adjacent the groove, notch or score mark 32 provides a contrasting image or tactile indicator of the location of the groove notch or score mark 32 of the lag screw 10 relative to the intramedullary nail 14.

The lag screw 10 may include a plurality of grooves, notches, or score marks 32 with corresponding indicia 46 to allow separation of differing segments 44 of the proximal section 30 as dictated by the extend of protrusion of the lag screw 10 from the femur 12.

Figure 4:
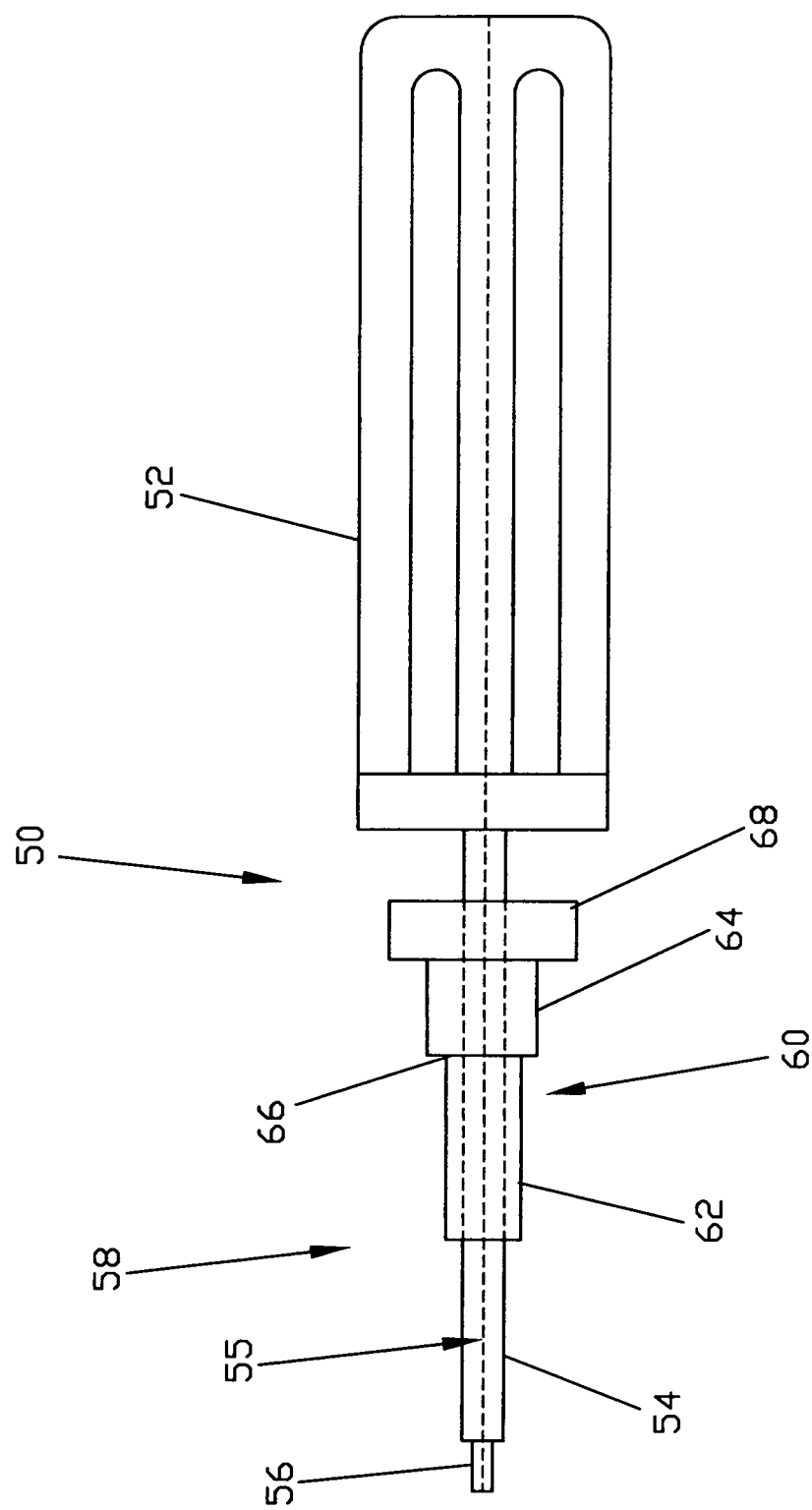
FIG. 4 is a side view of the driver of the present invention.

FIG. 4 depicts a multi-part driver generally indicated as 50 for use in combination with the lag screw 10 to selectively remove or separate at least a portion of the proximal section 30 protruding from the fractured femur 12 as shown in FIG. 2. The plurality of grooves, notches or score marks 32 allows for separation of only the portion(s) of the proximal section 30 as previously described.

Figure 5:
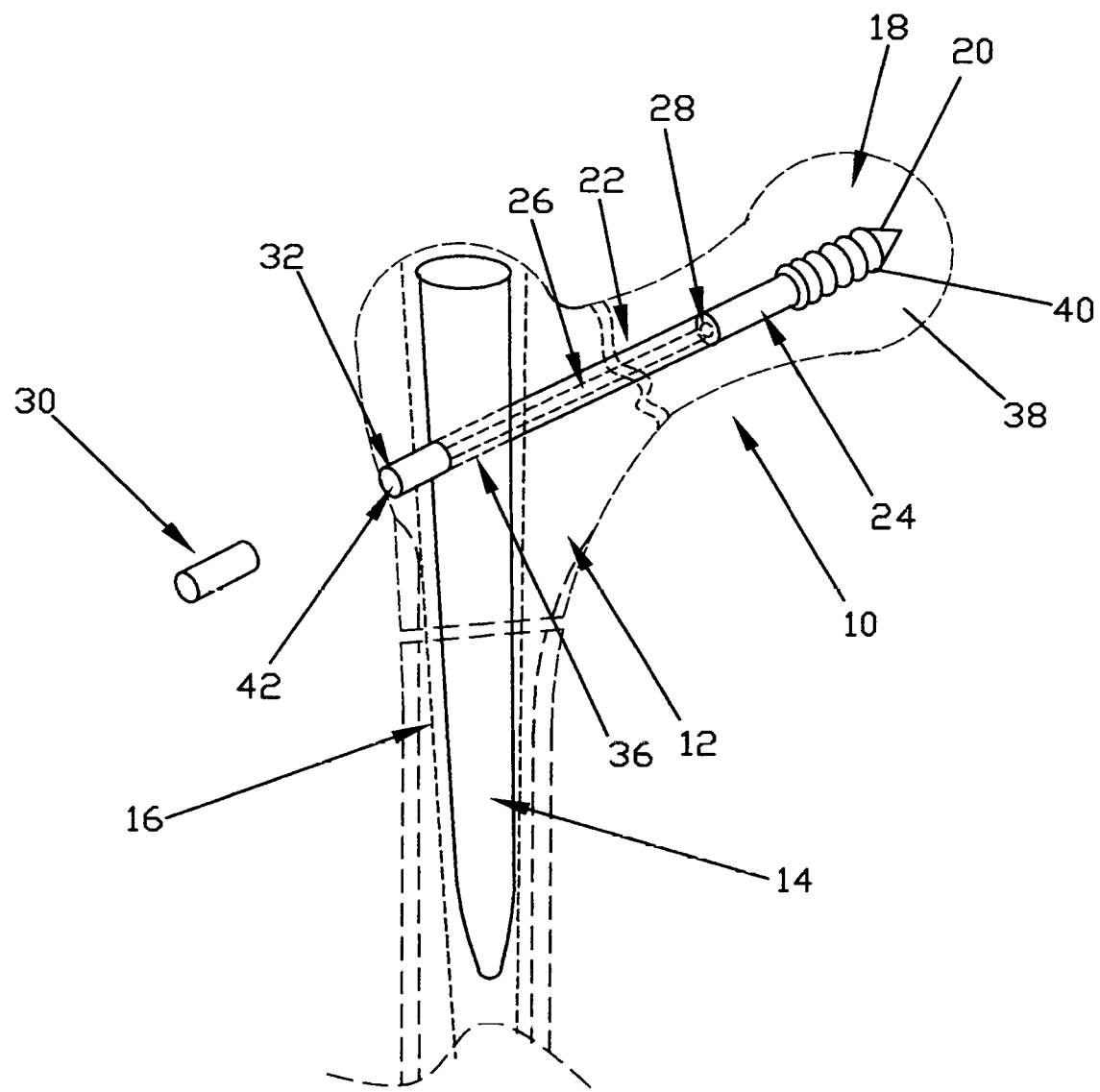
FIG. 5 is a perspective view of the lag screw of the present invention with the proximal section separated from the intermediate section.

The multi-part driver 50 comprises a handle 52 having an elongated cannulated shaft 54 having a cross-sectional dimension or diameter less than the cross-section dimensions or diameters of first channel 26 and second channel 42 includes a passageway 55 extending outwardly from the distal portion thereof including a first or inner driver member 56 formed on the outer end or tip thereof to engage the driver engagement member or element 28 formed in the distal end of the channel 26 formed in the intermediate section 22. A second or outer drive member generally indicated as 58 comprising a sleeve or substantially solid member 60 rotatably disposed on the elongated cannulated shaft 54. The second or outer drive member 58 includes a distal segment 62 having an outside diameter sized to press-fit into the proximal section 30 and an enlarged proximal segment 64 including a shoulder or stop 66 to engage the outer end 44 of the proximal section 30 when the multi-part driver 50 is operatively positioned relative to the lag screw 10 to remove the proximal section 30. A knurled knob 68 may be formed on the proximal end portion of the substantially solid member or sleeve 60 to facilitate rotation of the second or outer drive member 58 when the distal segment 62 of the substantially solid member or sleeve 60 is press-fit into the proximal section 30 to apply torque to the groove, notch or score mark 32 to separate the proximal section 30 from the externally threaded distal section 18 and intermediate section 22 as shown in FIG. 5.

Figure 6:
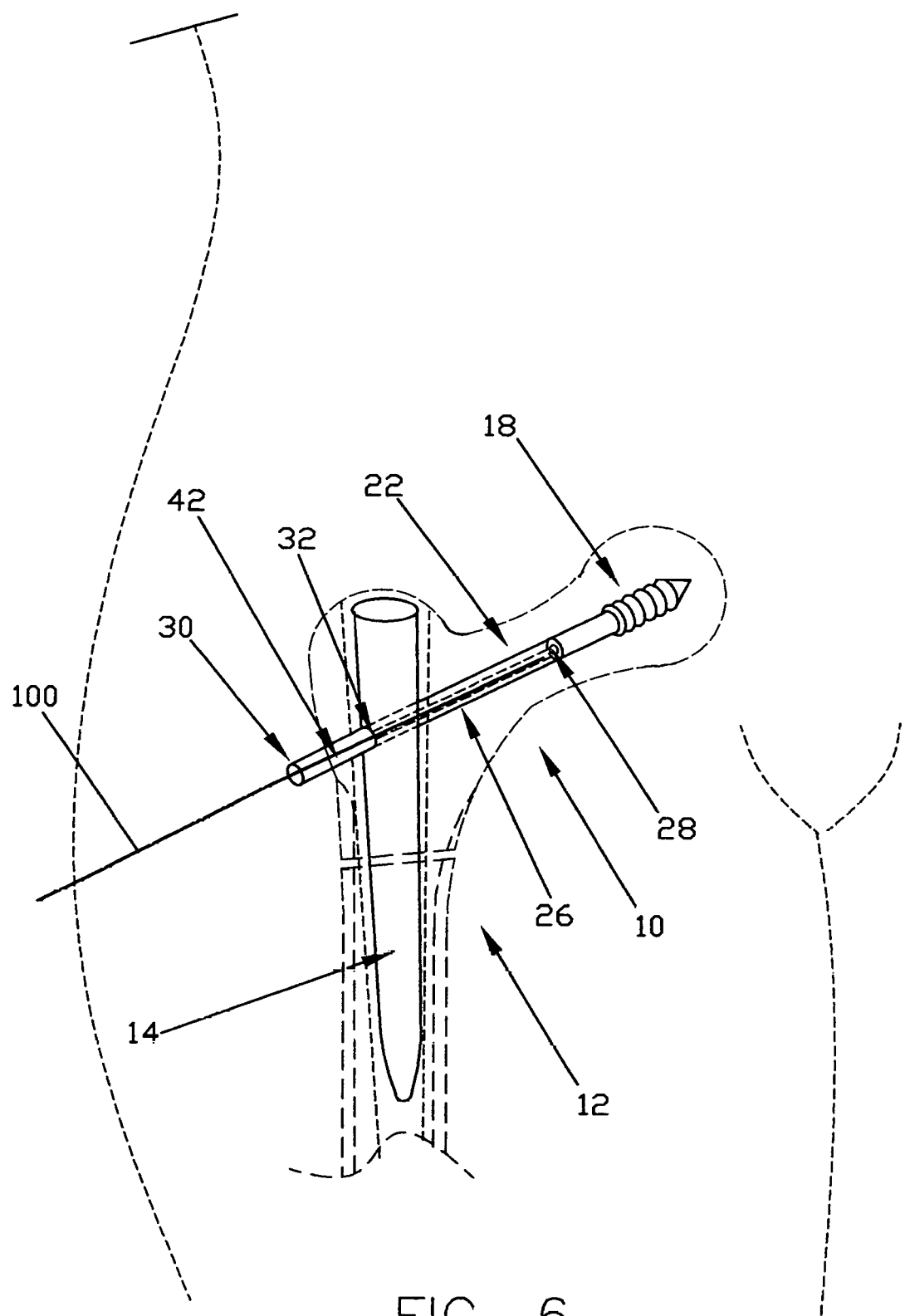
FIG. 6 is a perspective view of the lag screw of the present invention with a guide wire inserted through an incision into the lag screw.
Figure 7:
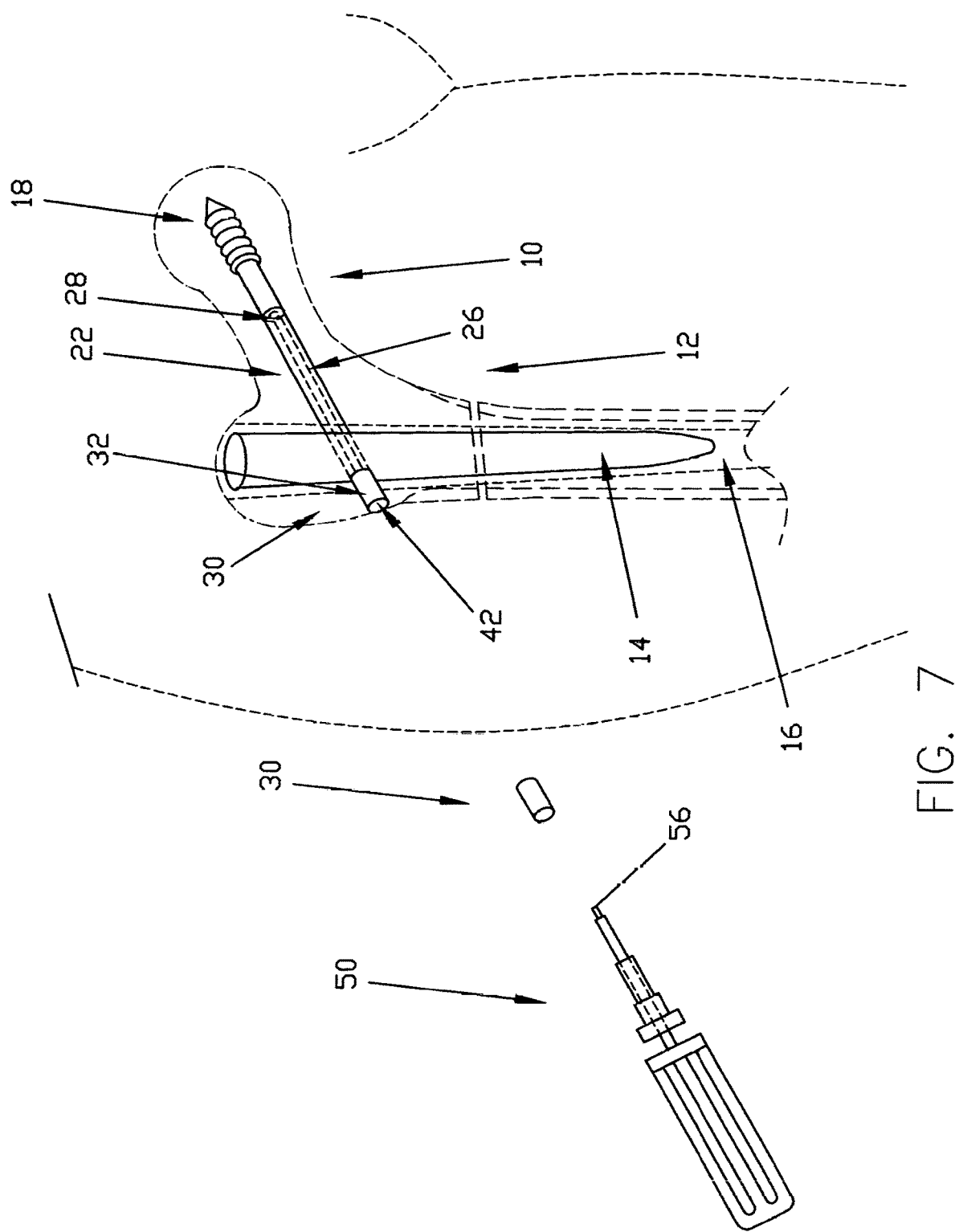
FIG. 7 is a perspective view of the lag screw and driver of the present invention with the proximal section separated from the intermedullary section of the present invention.

As shown in FIGS. 6 and 7, the percutaneous method of removing the outer portion of the proximal end of a lag screw 10 comprising an externally threaded distal section 18 embedded in the fractured femur 12, an intermediate section 22 having a substantially smooth surface 24 and including a channel 26 in the proximal portion thereof with a driver recess 28 formed in the distal end thereof and a proximal section 30 including a channel 42 axially aligned with the channel 26 of the intermediate section 22, and at least one groove, notch or score mark 32 formed in the exterior surface 34 of the lag screw 10 separating or between the intermediate section 22 and the proximal section 30 protruding from a fractured femur 12 using a multi-part driver 50 including a passageway 55 formed therethrough comprising an elongated cannulated shaft 54 extending outwardly therefrom including a first or inner drive member 56 formed on the outer end thereof to engage the driver engagement member or element 28 formed in the distal end of the channel 26 in the intermediate section 22 and a second or outer drive member 58 including a substantially solid member or sleeve 60 rotatably disposed on the elongated cannulated shaft 54 having a distal segment 62 with an outside diameter to press-fit into at least a portion of the proximal section 30, the method comprising the steps of:

making a small incision 100 in the skin adjacent to the proximal end of the lag screw 10, inserting a guide wire 102 through incision 100 of the channel 42 of the proximal section 30 and into the channel 26 of the intermediate section 22 the lag screw 10, aligning the passageway 104 of the elongated cannulated shaft 54 with the guide wire 102, sliding the elongated cannulated shaft 54 of the multi-part driver 50 along the guide wire 102 until the first or inner drive member 56 engages the first driver engagement or element 28 formed in the distal end of the channel 26 in the intermediate section 22 and press-fitting at least a portion of the second or outer drive member 58 within the proximal section 30, removing the guide wire 102 from the patient, holding the first or inner drive member 56 of the elongated cannulated shaft 54 in operative engagement with the first drive engagement or element 28 to prevent the intermediate section 22 and externally threaded distal section 18 from rotating, while twisting or rotating the second or outer drive member 58 of the multi-part driver 50 relative to the lag screw 10 to generate a torque on the proximal section to break or separate the proximal section 30 from the intermediate section 22 and externally threaded distal section 18 of the lag screw 10 along the groove, notch or score mark 32, withdrawing the multi-part driver 50 and the separated proximal section 30 of the lag screw 10 from the patient, and closing the incision 100.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A multi-part driver and lag screw to remove an outer portion of a proximal end of a lag screw protruding from a fractured femur when embedded in the femur to stabilize an intramedullary nail implanted in the intramedullary canal, said lag screw comprises a distal section, an intermediate section including a channel formed in a proximal portion thereof with a driver engagement member in the shape of a slot or recess formed at a distal end thereof, and a proximal section having a plurality of notches, grooves or score marks formed on the exterior surface of said lag screw separating or between said intermediate section and said proximal section and said multi-part driver comprises a first driver member formed thereon configured to engage said driver engagement member to prevent said distal section and intermediate section from rotating in a femoral head when torque is applied to said proximal section by a second driver member engaging said proximal section of said lag screw to separate at least a portion of said proximal section from said distal section and said intermediate section along one of the notches, grooves or score marks wherein said distal section comprises external threads configured to be secured in a channel tapped into a femur femoral head and said intermediate section includes a smooth exterior surface configured to be at least partially disposed within a channel formed through an upper portion of the intramedullary nail, said channel being formed on a proximal end of said intermediate section having said driver member formed on an inner end thereof to operatively receive said first driver member formed on said multi-part driver and said proximal section includes a channel coaxially aligned with said channel of said intermediate section and said multi-part driver comprises a handle having a shaft having a cross-sectional dimension or diameter less than cross-section dimensions or diameters of said channel of said intermediate section and said channel formed in said proximal section extending outwardly from a distal portion thereof and said first driver member formed on an outer end thereof to engage said driver engagement member formed in said distal end of said channel formed in said intermediate section and a second drive member comprises a member rotatably disposed on said cannulated shaft, said second drive member includes a distal segment having an outside diameter sized to press-fit into at least a portion of said proximal section to twist said proximal section to separate at least a portion of said proximal section from said distal section and said intermediate section.

2. The multi-part driver and lag screw of claim 1 further including an indicia disposed adjacent each said groove, notch or score mark provides an image or indicator of the location of each said groove, notch or score mark of the lag screw relative to the intramedullary nail.

\* \* \* \* \*